United States Patent

Takei et al.

[11] Patent Number: 5,981,679
[45] Date of Patent: Nov. 9, 1999

[54] ORGANOPOLYSILOXANE

[75] Inventors: Masao Takei; Akira Sumi; Kaoru Kimura; Hiroshi Suzuki; Takenao Hattori, all of Nagoya, Japan

[73] Assignee: Toagosei Co., Ltd., Tokyo, Japan

[21] Appl. No.: 08/953,436

[22] Filed: Oct. 17, 1997

[30] Foreign Application Priority Data

Nov. 18, 1996 [JP] Japan ................................. 8-323621
Dec. 2, 1996 [JP] Japan ................................. 8-337503

[51] Int. Cl.$^6$ ..................................................... C08G 77/08
[52] U.S. Cl. .................................. 528/15; 528/31; 528/32; 526/279
[58] Field of Search .......................... 528/15, 31, 32; 526/279

[56] References Cited

U.S. PATENT DOCUMENTS 4,301,268  11/1981  Kropac .
5,057,578  10/1991  Spinelli ................................. 528/280
5,331,067   7/1994  Seidner et al. ....................... 525/479

FOREIGN PATENT DOCUMENTS 2-045533   2/1990   Japan .

OTHER PUBLICATIONS

Kokko, Bruce J., "Silicon acrylated through the hydrosilation of polyacryloyloxy functional monomers with copolymers of dimethyl and hydrogen methysiloxanes.", Jour. App. Poly. Sci., vol. 47, pp. 1309–1314 (1993).

*Primary Examiner*—Melvyn I. Marquis
*Attorney, Agent, or Firm*—Browdy and Neimark

[57] ABSTRACT

The present invention provides an organopolysiloxane having acryloyl groups or methacryloyl groups at both terminals thereof, where silicon atoms at both terminals of the organopolysiloxane are each independently added to double bonds each of acryloyl groups or methacryloyl groups of compounds each having at least two acryloyl groups or methacryloyl groups; a curable resin composition comprising such an organopolysiloxane; and a process for producing such an organopolysiloxane comprising adding a compound having at least two acryloyl groups or methacryloyl groups to an organopolysiloxane having SiH groups at only both terminals thereof. The curable resin composition has distinguished transparency, luster, peelability, surface lubricity and water and oil repellency, and therefore is useful as a resin for mold-releasable paper, a coating agent, an anticorrosive agent for printed substrate, etc.

23 Claims, 2 Drawing Sheets

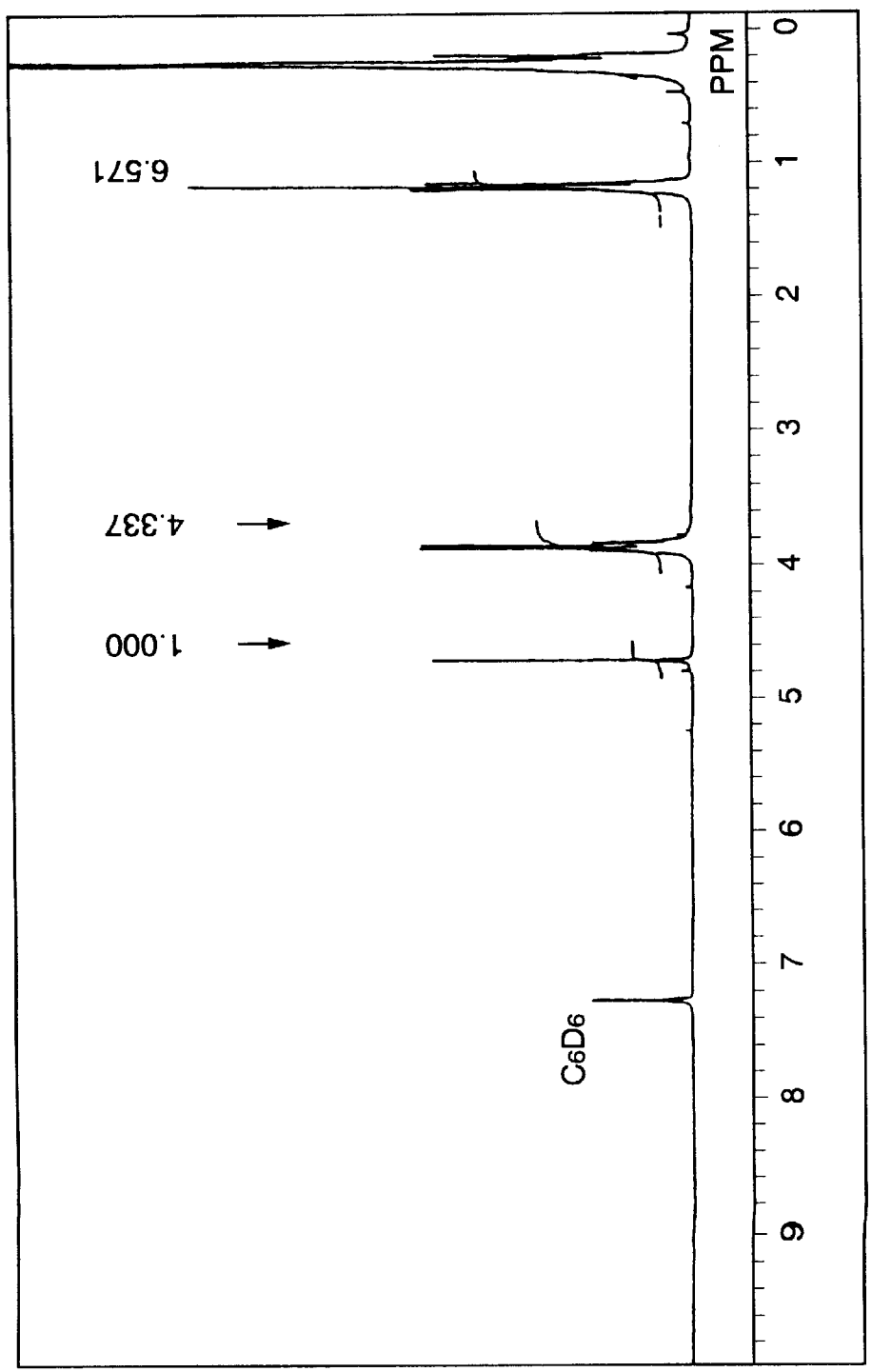

ORGANOPOLYSILOXANE

BACKGROUND OF THE INVENTION

1. Field of the Invention

The present invention relates to a novel organopolysiloxane, a process for producing the same and a curable resin composition containing the organopolysiloxane as an effective component. A curable resin composition containing the novel organopolysiloxane as an effective component has distinguished transparency, luster, peelability, surface lubricity and water and oil repellency, and therefore is useful as a resin for mold-releasable paper, a coating agent, an anticorrosive agent for printed substrates, etc.

2. Related Art Statement

Organopolysiloxanes having acryloyl groups or methacryloyl group (both groups together being hereinafter referred to as (meth) acryloyl groups) at the terminals thereof and/or as side chains are distinguished in polymerization reaction and UV curing, and thus are used as a resin for mold-releasable paper, a coating agent, an anticorrosive agent for printed substrates, etc.

It has been known that these organopolysiloxanes can be produced by reaction of, for example, a tri(meth)acrylate compound having —COH groups with an organopolysiloxane having SiZ groups, where Z is an alkoxy group, a hydroxy group or a chlorine atom (U.S. Pat. No. 4,301,268).

However, the organopolysiloxanes so produced have SiOC— bonds and thus are liable to be hydrolyzed.

A process for producing an organopolysiloxane by reaction of (meth) acrylic acid with an organopolysiloxane having epoxy groups in the molecule has been also known (JP-A-2-45533). However, the process has a difficulty in reaction control due to a very large heat of reaction.

It has been also known to produce organopolysiloxanes by hydrosilylation reaction of an organopolysiloxane having SiH groups with (meth)acryloyl groups of a compound having a plurality of (meth)acryloyl groups (the compound being hereinafter referred to as (meth)acrylate compound) in the presence of a platinum catalyst [Journal of Applied Polymer Science, 47, 1309–1314 (1993)]. However, the hydrosilylation reaction is applied to a dimethylsiloxane-methylhydrogen siloxane copolymer as shown by the following formula (IV) (which will be hereinafter referred to as PDMHMS), that is, an organopolysiloxane having SiH groups as side chains:

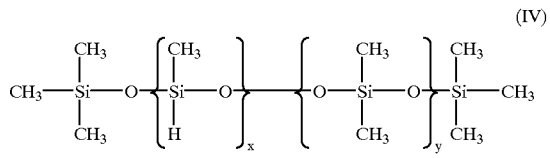

Thus, the hydrosilylation reaction produces only organopolysiloxanes having (meth)acryloyl groups as side chains and further has the following problem.

That is, the starting material PDMHMS is a copolymer and the number and positions of the SiH groups in one molecule are largely fluctuated, and thus it is hard to control the hydrosilylation reaction and also to control the properties of the resulting organopolysiloxanes. Furthermore, the PDMHMS used in the hydrosilylation reaction is less compatible with the (meth)acrylate compound, and thus a relatively large amount of the catalyst is required for satisfactory hydrosilylation reaction. Particularly when a trimethylolpropane triacrylate (which will be hereinafter referred to as TMPTA) useful for endowing the resulting organopolysiloxanes with various properties is used as the (meth)acrylate compound, it is necessary to use an organic solvent besides the large amount of the catalyst. In that case, the resulting organopolysiloxanes often become white turbid and thus are very inconvenient for use, for example, as a coating material.

OBJECT AND SUMMARY OF THE INVENTION

An object of the present invention is to provide a novel organopolysiloxane having (meth)acryloyl groups at both terminals thereof. By using a specific organopolysiloxane having a good compatibility with a (meth)acrylate compound as a starting material, an organopolysiloxane having (meth)acryloyl groups at both terminals thereof can be readily produced. That is, the organopolysiloxane having (meth)acryloyl groups at both terminals thereof so produced has an improved compatibility with a (meth)acrylate compound and a distinguished curability.

Another object of the present invention is to provide a novel curable resin composition containing an organopolysiloxane having (meth)acryloyl groups at both terminals thereof as an effective component.

The present inventors found that these objects could be attained by use of a relatively low molecular weight, $\alpha,\omega$-type polysiloxane having hydrogen atoms on the terminal silicons, and established the present invention.

That is, the present invention provides an organopolysiloxane having (meth)acryloyl groups at both terminals thereof, where silicon atoms at both terminals of the organopolysiloxane are each independently added to the double bonds each of (meth)acryloyl groups of (meth)acrylate compounds each having at least two (meth)acryloyl groups.

Furthermore, the present invention provides an organopolysiloxane having (meth)acryloyl groups at both terminals thereof, as shown by the following structural formula (I):

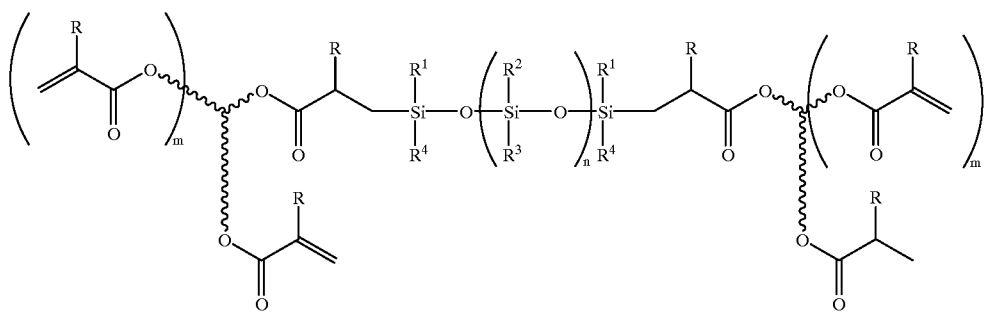

(I)

where R is a methyl group or a hydrogen atom; $R^1$ and $R^4$ are each independently an alkoxy group, an aryloxy group, an alkyl group, a cycloalkyl group or an aryl group; $R^2$ and $R^3$ are each independently an alkyl group, a cycloalkyl group or an aryl group; n is a positive number of 1 to 10,000; and m is 0 or a positive number of at most 10.

Furthermore, the present invention provides a curable resin composition comprising an organopolysiloxane having (meth)acryloyl groups at both terminals thereof, where silicon atoms at both terminals of the organopolysiloxane are each independently added to the double bounds each of (meth)acryloyl groups of (meth)acrylate compounds each having at least two (meth)acryloyl groups.

BRIEF DESCRIPTION OF THE DRAWINGS

FIG. 2 is an NMR chart of an organopolysiloxane having SiH groups only at both terminals thereof, produced according to Synthesis Example 1 shown in the present specification.

DETAILED DESCRIPTION OF THE INVENTION

Figure 1:
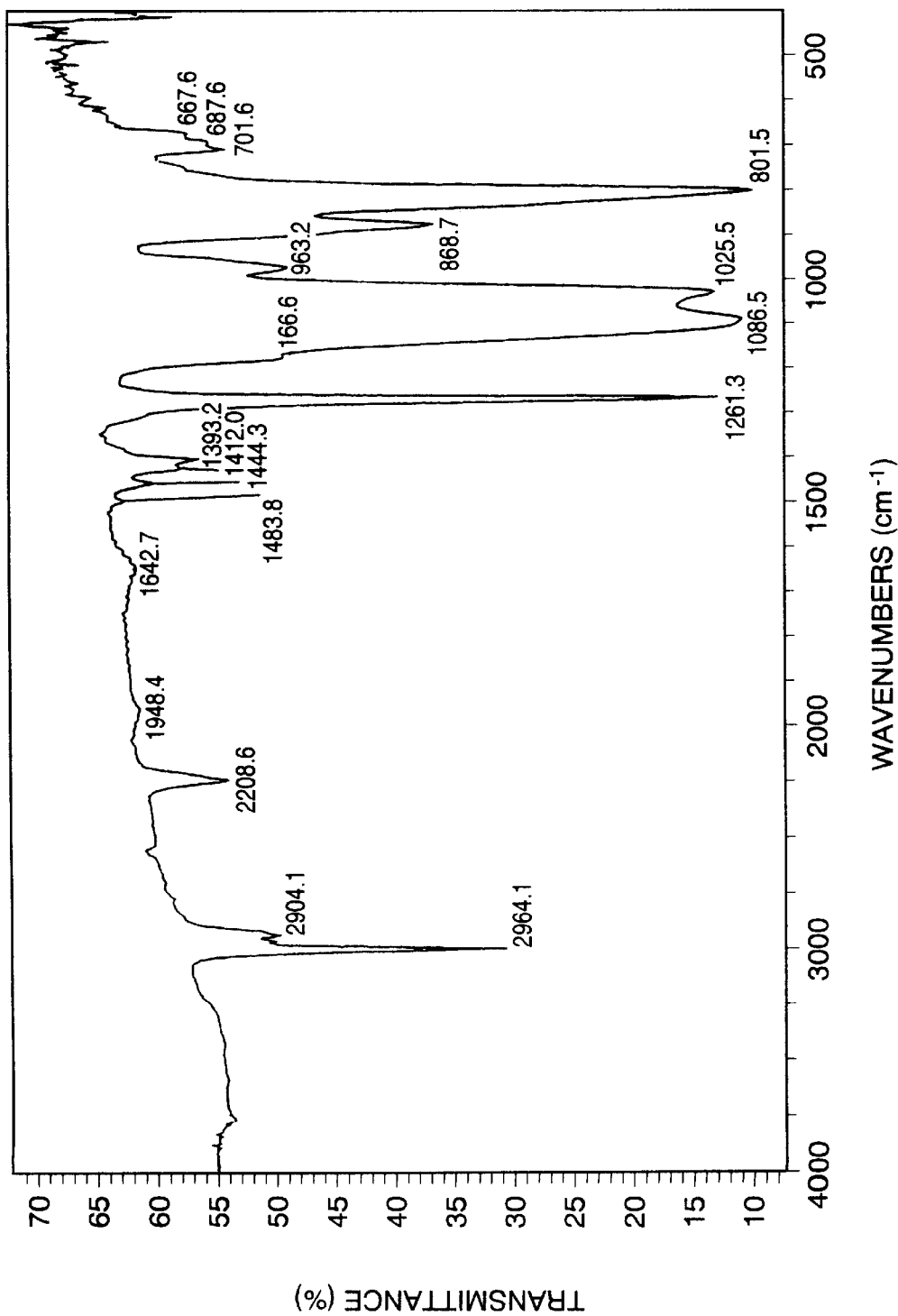
FIG. 1 is an IR chart of an organopolysiloxane having SiH groups only at both terminals, produced according to Synthesis Example 1 shown in the present specification.

In the present organopolysiloxane, silicon atoms at both terminals thereof are each independently added to the double bonds each of (meth)acryloyl groups of (meth)acrylate compounds each having at least two (meth)acryloyl groups. Therefore, the present organopolysiloxane has (meth)acryloyl groups at both terminals thereof. The bonds formed by addition of silicon atoms each to the double bonds of (meth)acryloyl groups typically have the following structure:

-silicon atom-ethylene group or propylene group -carbonyl group-

Specific examples of the present organopolysiloxane includes an organopolysiloxane having acryloyl groups at both terminals thereof, where silicon atoms at both terminals of the organopolysiloxane are each independently added to the double bonds each of acryloyl groups of compounds each having at least two acryloyl groups as shown by the following structural formula (II):

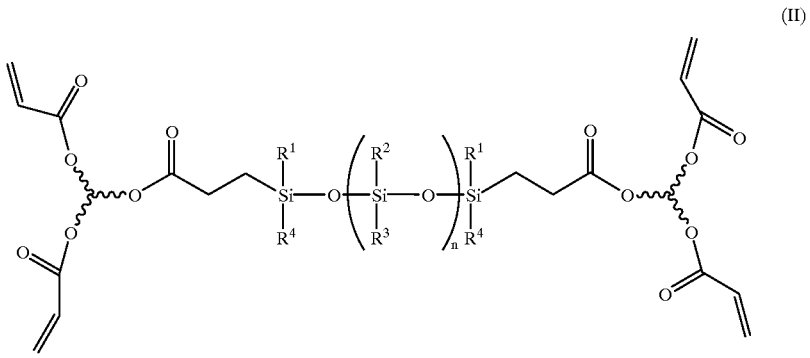

(II)

where $R^1$ and $R^4$ are each independently an alkoxy group, an aryloxy group, an alkyl group, a cycloalkyl group or an aryl group; $R^2$ and $R^3$ are each independently an alkyl group, a cycloalkyl group or an aryl group; and n is a positive number of 1 to 10,000.

The alkoxy group includes, for example, methoxy, ethoxy, n- and iso-propoxy, n-, i- and t-butoxy, etc., and the aryloxy group includes, for example, phenoxy, etc. The alkyl group includes, for example, methyl, ethyl, n-and i-propyl, n-, i- and t-butyl, etc. and the cycloalkyl group includes, for example, cyclohexyl, etc. The aryl group includes, for example, phenyl, etc.

The compounds shown by the formulae (I) and (II) each contain two $R^1$ groups in one molecule, where the $R^1$ groups may be the same or different from each other. Similarly two $R^4$ groups contained in one molecule may be the same or different from each other. Furthermore, the $R^1$ and $R^4$ groups may be the same or different from each other.

In the formulae (I) and (II), $R^2$ and $R^3$ are each independently an alkyl group, a cycloalkyl group or an aryl group. For the alkyl group, the cycloalkyl group and the aryl group, those exemplified above for $R^1$ and $R^2$ can be used. $R^2$ and $R^3$ may be the same or different from each other. Furthermore, n $R^2$ groups contained in one molecule may be all the same groups or two or more different groups. This is also applicable to the $R^3$ groups.

For $R^1$ to $R^4$ in the formulae (I) and (II), appropriate groups may be selected in view of properties required for the organopolysiloxane. Above all, compounds, whose $R^2$ and $R^3$ are methyl and/or ethyl, are preferable, because they can be produced from cheap starting materials and are liable to endow the organopolysiloxane with the so-called silicone characteristics such as peelability, surface lubricity, water and oil repellency, etc. Compounds, whose $R^2$ and $R^3$ are all methyl, are more preferable. Furthermore, compounds, whose two $R^1$s and two $R^4$s in one molecule are the same, respectively, are preferable, because of easy synthesis of the compounds, and compounds, whose two $R^1$s and two $R^4$s are all the same group, are more preferable.

Furthermore, compounds whose $R^1$s are an alkoxy group or an aryloxy group, i.e. compounds shown by the formulae (I) and (II), whose terminal silicons each have at least one alkoxy group and/or aryloxy group, are particularly preferable in the present invention because of the compatibility with the (meth)acrylate compound, and furthermore organopolysiloxanes shown by the formulae (I) and (II), whose $R^1$ and $R^4$ are each an alkoxy group or an aryloxy group, are more preferable. Compounds, whose $R^1$s and $R^4$s are ethoxy, are particularly preferable because of a low toxicity.

In the formulae (I) and (II), n is a positive number of 1 to 10,000, preferably 10 to 100. When n exceeds 100, the compatibility with the (meth)acrylate compound will be lowered, resulting in the necessity for a larger amount of a catalyst or solvent in the production and furthermore resulting in production of undesirable white turbid organopolysiloxanes. In view of the compatibility with the (meth)acrylate compound, it is preferable that n is not more than 50, and it is more preferable that n is not more than 30. Furthermore, in order to provide the organopolysiloxane with the silicone characteristics, it is preferable that n is not less than 10.

The following processes are preferable in the production of the present organopolysiloxane:

A first process for producing an organopolysiloxane having (meth)acryloyl groups at both terminals thereof comprises adding an organopolysiloxane represented by the following structural formula (III) to a compound having at least two (meth)acryloyl groups:

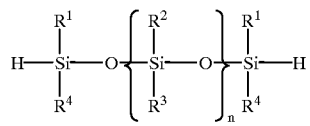

(III)

where $R^1$, $R^2$, $R^3$ and $R^4$, and n have the same meanings as defined above.

In the first process, the organopolysiloxane has SiH groups at only both terminals thereof in one molecules, as shown by the formula (III), and thus the hydrosilylation reaction takes place only at both terminals thereof. That is, the structures of the resulting organopolysiloxanes and their cured products can be more easily designed than in the above-mentioned conventional process using PDMHMS capable of containing a large number of SiH groups in one molecule.

Compounds shown by the formula (III), for example, compounds whose $R^1$ and $R^4$ are each an alkoxy group or an aryloxy group in the formula (III), can be obtained by condensation reaction of polysiloxane-α,ω-diol with trialkoxy (or triaryloxy) silane as shown by the following reaction equation (V):

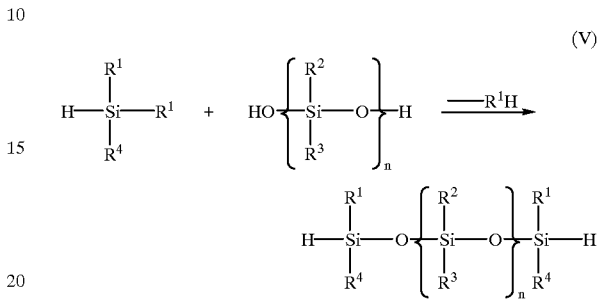

(V)

It is preferable to carry out the reaction with excess of trialkoxy (or triaryloxy) silane. The reaction can be carried out in the presence or absence of a transesterification catalyst such as p-toluenesulfonic acid or trifluoroacetic acid. The reaction in the absence of the catalyst can unnecessitate a further step of removing the catalyst by ion exchange resin, etc. after the end of reaction. That is, compounds of formula (III) can be produced through more simple process steps.

In the reaction shown by the foregoing reaction equation (V), it is preferable that $R^1$, $R^2$, $R^3$ and $R^4$ are each an alkoxy group having 1 to 8 carbon atoms or an aryloxy group, an alkyl group or an aryl group, particularly methoxy, ethoxy, propoxy (inclusive of n-propoxy and i-propoxy) or butoxy (inclusive of n-, i- and t-butoxy).

In the polysiloxane-α,ω-diol, $R^2$ and $R^3$ may be the same or different from each other, and n $R^2$s contained in one molecule may be all the same groups or two or more different groups. This is also true of $R^3$.

In the trialkoxysilane, the three alkoxy groups may be all the same groups or two or three different groups, but to obtain a desired compound with a good purity it is preferable that the three alkoxy groups are all the same groups.

In the reaction equation (V), n is a positive number of 1 to 10,000, preferably 1 to 1,000, more preferably 5 to 200, and most preferably 10 to 100 from the viewpoint of reactivity. When n exceeds 10,000, the viscosity of reaction solution will be too high to conduct the reaction smoothly, or the condensation reaction rate of polysiloxane-α,ω-diol with trialkoxysilane will be lowered, resulting in unsatisfactory production efficiency.

The reaction is a condensation reaction and thus can be carried out under conditions of ordinary condensation reaction, which depend on kinds of substituents $R^1$ to $R^4$ of siloxanes and alkoxysilanes. Generally reaction temperature is preferably 20° to 100° C., more preferably 40° to 80° C.; reaction time is preferably 1 to 20 hours, more preferably 2 to 8 hours; and reaction pressure may be atmospheric, superatmospheric or subatmospheric, but it is preferable to use the atmospheric pressure from the viewpoint of simplification of apparatus structures and easy operations in the production. It is also preferable to conduct the reaction in an inert gas atmosphere.

In the foregoing reaction, one mole of polysiloxane-α,ω-diol reacts with two moles of trialkoxysilane. To suppress side reactions, it is preferable to conduct the reaction with excess or more preferably large excess of trialkoxysilane. Specifically, it is preferable to conduct the reaction in a molar ratio of polysiloxane-α,ω-diol to trialkoxysilane of 1:3 or more or more preferably 1:5 or more.

It is preferable to conduct the reaction in the absence of the catalyst, as mentioned above, but the reaction may be accelarated with an ordinary transesterification catalyst, etc.

The catalyst includes, for example, metal compound catalysts such as $Ti(OEt)_4$, $Ti(OBu)_4$, $Ti(OPr)_4$, $SnO$, $Sn(COO)_2$, $Bu_2SnO$, $Bi(OH)_3$, $Zn(CH_3COO)_2.2H_2O$, $Pb(CH_3COO)_2.3H_2O$, $Pb(C_6H_5COO)_2.H_2O$, $PbO$, $Sn_2O_3$, $Al(CH_3COO)_3$, $Mn(CH_3COO)_2.4H_2O$, $Co(CH_3COO)_2.4H_2O$, $Cd(CH_3COO)_2$, $Cd(COO)_2$, dibutyl tin laurate, dibutyl tin dimaleate, dibutyl tin thiocarboxylate, dioctyl tin mercaptide, stannous octanoate, lead octenoate, etc.; triethylenediamine tetramethylguanidine, 2-(dimethylaminomethyl) phenol, N,N,N',N'-tetramethylhexane-1,6-diamine, 1,8-diazabicyclo [5.4.0] undecene-7, p-toluenesulfonic acid, trifluoroacetic acid, etc., among which p-toluenesulfonic acid and trifluoroacetic acid are preferable.

It is preferable to use 0.1 to 5% by weight of the catalyst on the basis of total amount of polysiloxane-α,ω-diol and trialkoxysilane.

It is preferable to conduct the reaction without any solvent, but to control the reaction easily or lower the viscosity of the reaction solution, an organic solvent may be used. As the organic solvent, those which can dissolve the starting materials and the product and which are inert under the reaction conditions can be used. They preferably include, for example, diethyl ether, tetrahydrofuran, acetone, methylethylketone, benzene, toluene, xylene, hexane, mineral spirits, etc.

By addition reaction between the thus obtained organopolysiloxane having SiH groups at both terminals thereof, as shown by the formula (III), and (meth)acrylate compounds each having at least two (meth)acryloyl groups, the present organopolysiloxanes can be obtained, and thus description will be made of the addition reaction below:

The addition reaction is a hydrosilylation reaction between the SiH groups at both terminals of the compound of formula (III) and the (meth)acryloyl groups of (meth)acrylate compounds, which proceeds in the presence of a catalyst of the Group VIII metal, etc.

The (meth)acrylate compound for use in the reaction includes, for example, diethyleneglycol di(meth)acrylate, triethyleneglycol di(meth)acrylate, tetraethyleneglycol di(meth)acrylate, nonaethyleneglycol di(meth)acrylate, dipropyleneglycol di(meth)acrylate, tripropyleneglycol di(meth)acrylate, tetrapropyleneglycol di(meth)acrylate, polypropyleneglycol di(meth)acrylate, 1,4-butanediol di(meth)acrylate, 1,5-pentanediol di(meth)acrylate, 1,6-hexanediol di(meth)acrylate, 1,9-nonanediol di(meth)acrylate, neopentylglycol di(meth)acrylate, neopentylglyol ethyleneoxide (ethyleneoxide being hereinafter referred to as EO)-modified di(meth)acrylate, neopentylglycol propyleneoxide (propyleneoxide being hereinafter referred to as PO)-modified di(meth)acrylate, bisphenol A/EO-modified di(meth)acrylate, bisphenol A/PO-modified di(meth) acrylate, hydrogenated bisphenol A/EO-modified di(meth) acrylate, hydrogenated bisphenol A/PO-modified di(meth) acrylate, trimethylolpropane di(meth)acrylate, trimethylolpropane EO-modified di(meth)acrylate, trimethylolpropane PO-modified di(meth)acrylate, glycerine di(meth)acrylate, glycerine EO-modified di(meth)acrylate, glycerine PO-modified di(meth)acrylate, trimethylolpropane tri(meth)acrylate, trimethylolpropane EO-modified tri (meth)acrylate, trimethylolpropane PO-modified tri(meth) acrylate, glycerine tri(meth)acrylate, glycerine EO-modified tri(meth)acrylate, glycerine PO-modified tri(meth)acrylate, pentaerythritol EO-modified tetra(meth)acrylate, pentaerythritol PO-modified tetra(meth)acrylate, ditrimethylolpropane tetra(meth)acrylate, pentaerythritol tri(meth) acrylate, pentaerythritol EO-modified tri(meth)acrylate, pentaerythritol PO-modified tri(meth)acrylate, ditrimethylolpropane tri(meth)acrylate and trimethylolpropane allylether di(meth)acrylate, etc. In addition, any of compounds, if they have at least two (meth)acrylol groups, can be used without any particular limitation, but it is preferable that such compounds have no hydroxyl group in the molecules, and furthermore such compounds having not more than 11 (meth)acryloyl groups are preferable from the viewpoints of reactivity and curability. Among them, trimethylolpropane PO-modified triacrylate and trimethylolpropane allylether diacrylate are preferable. These (meth) acrylate compounds are preferable particularly because of their good compatibility with the compounds shown by the formula (III) and the resulting organopolysiloxanes of the present invention.

The catalyst of the group VIII metal includes, for example, metallic simple substances, organometallic complexes, metallic salts and metallic oxides of the group VIII metal such as cobalt, nickel, ruthenium, rhodium, palladium, iridium, platinum, etc., among which metallic simple substance, organometallic complexes, metallic salts and metallic oxides of platinum are preferable because of high catalytic activity and easy handling and organoplatinum complexes are particularly preferable. It is preferable to use 0.1 to 5% by weight of the catalyst on the basis of total amount of the compound shown by the formula (III) and the (meth)acrylate compound.

Other reaction conditions for the hydrosilylation reaction are not particularly limited, but preferable reaction temperature is 20° to 80° C. and preferable reaction time is 2 to 10 hours.

Examples of curable resins formed by hydrosilylation reaction with a compound having three acryloyl groups as a polyfunctional (meth)acrylate compound are schematically shown by the following formulae (VI) and (VII), where formula (VI) is identical with formula (II):

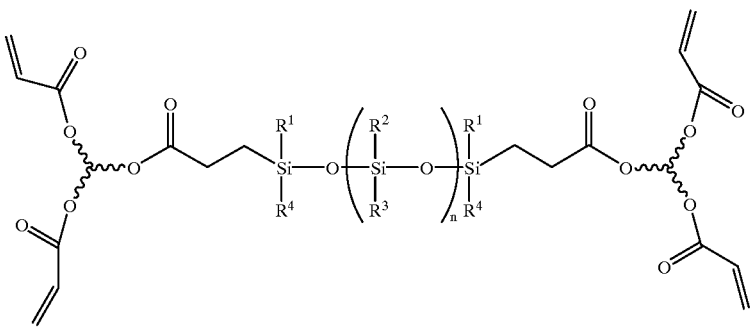

(VI)

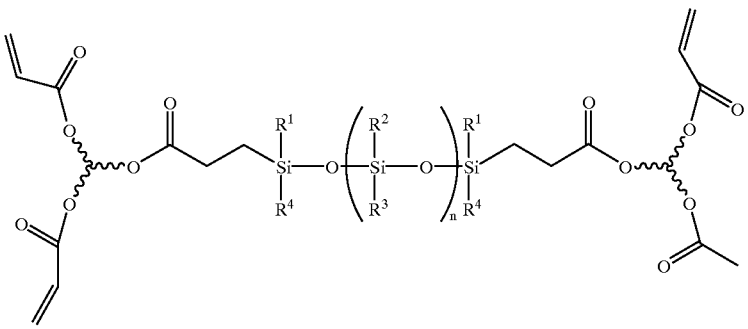

(VII)

In this case, there is a possibility of simultaneous production of the organopolysiloxane shown by the formula (VI) and the organopolysiloxane shown by the formula (VII), but a ratio of these products can be adjusted by a ratio of the compound shown by the formula (III) to the (meth)acrylate compound as charged. For example, by charging excess, preferably large excess in moles of the (meth)acrylate compound over the SiH groups of the compound shown by the formula (III), the organopolysiloxane shown by the formula (VI) can be predominantly obtained. The reaction under such a condition as excess of (meth)acrylate compound is preferable also from the viewpoint of inhibition of gelation during the reaction.

A second process for producing the present organopolysiloxane is a process which comprises allowing a compound having at least one (meth)acrylol group as a reaction product of a (meth)acrylate compound having at least two (meth)acryloyl groups with a hydrosilane compound represented by the following formula (VIII) to react with an organopolysiloxane having hydroxyl groups at both terminals thereof:

$$H_aSiR_bX_{4-(a+b)} \quad (VIII)$$

where X is a halogen atom, an alkoxy group or an aryloxy group; R is an alkyl group, a cycloalkyl group, or an aryl group; a is 1 or 2; b is 0, 1 or 2; and a +b≦3; and when the number of Rs or Xs is 2 or more, Rs or Xs may be the same or different from each other.

Reaction between the (meth)acrylate compound and the hydrosilane compound is the same hydrosilylation reaction as in the first process and proceeds in the presence of a catalyst of the group VIII metal, etc.

(Meth)acrylate compounds and catalysts of the group VIII metal for use in the reaction are the same as mentioned before, and the amounts thereof and reaction conditions are also the same as mentioned before.

It is preferable to conduct the reaction between the (meth)acrylate compound and the hydrosilane compound in a ratio of the (meth)acryloyl groups of (meth)acrylate compound to the SiH groups of hydrosilane compound of N equivalent weights: (N−1) equivalent weights or less, where N is a real number of 2 or more.

The (meth)acrylate compounds for use in the reaction are the same as mentioned before, and the hydroxysilane compounds shown by the formula (VIII) include, for example, trimethoxysilane, triethoxysilane, tripropoxysilane, methyldimethoxysilane, ethyldimethoxysilane, dimethylmethoxysilane, diethylethoxysilane, triphenoxysilane, phenyldimethoxysilane, diphenylethoxysilane, cyclohexyldimethoxysilane, dimethoxydihydrosilane, diethoxydihydrosilane, dipropoxydihydrosilane, trichlorosilane, methyldichlorosilane, dimethylchlorosilane, ethyldichlorosilane, diethylchlorosilane, etc., among which alkoxy-containing hydrosilanes such as trimethoxysilane, triethoxysilane, methyldimethoxysilane, dimethylmethoxysilane, etc. are preferable for the reasons of easy handling, stability of reaction product, etc.

Reaction between the resulting reaction product having at least one (meth)acryloyl group and the organopolysiloxane having hydroxyl groups at both terminals thereof is a condensation reaction and can be carried out under the above-mentioned conditions for the condensation reaction.

The organopolysiloxane having hydroxyl groups at both terminals thereof includes, for example, polysiloxane-α,ω-diol having the above-mentioned repeating units.

When a hydrosilane compound having at least one halogen atom is used, the reaction product having at least one (meth)acryloyl group or a solution of the reaction product in the organic solvent at a concentration of 10 to 70% by weight is added at room temperature to a solution of the polyorganosiloxane and an acid receptor in the organic solvent at a concentration of 10 to 70% by weight, whereby the reaction immediately starts to proceed. After the end of reaction, the resulting acid receptor hydrohalegenide is filtered off, and then if necessary the filtrate is washed with water and the organic solvent is distilled off therefrom, whereby the present organopolysiloxane can be obtained. As the acid receptor, amines can be used, and, for example, pyridine, triethylamine, aniline, etc. are preferably used. It is preferable to use about 1.2 moles of the acid receptor per mole of hydrogen halide formed by the dehydrohalogenation reaction.

A third process for producing the present organopolysiloxane uses polysiloxane-α,ω-diol as an intermediate and includes a process [1] based on reaction of an alkoxysilane having acryloyl groups shown by the following formula [IX] and a process [2] based on reaction of an alkoxychlorosilane having acryloyl groups:

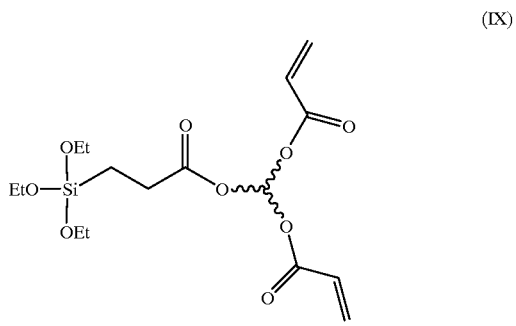

(IX)

According to the process [1], it is necessary to use a catalyst such as p-toluenesulfonic acid, etc. and a solvent to conduct condensation. By use of such an acid catalyst, dehydration reaction of Si-OH groups themselves can also take place as a side reaction besides the desired condensation reaction, and there would be such a possibility that the by-produced $H_2O$ reacts with the alkoxy group in an acidic atmosphere, resulting in condensation reaction of alkoxy groups themselves to form undesired compounds or to cause gelation of the reaction solution. Furthermore, a further step of removing the catalyst and solvent is required after the end of reaction, and thus the process will be complicated.

According to the process [2], it is difficult to remove hydrogen chloride by-produced during the reaction, and also there is a problem of corrosion of the apparatus by hydrogen chloride. In the first process, i.e. the process based on the hydrosilylation reaction only at both terminals of the organopolysiloxane of formula (III), on the other hand, such a side reaction can be prevented and no hydrogen chloride is generated, because such an acid catalyst is not used. Thus, the first process is distinguished in these points.

The present organopolysiloxane has at least one (meth) acryloyl group each at both terminals thereof and thus can be cured by heat, ultraviolet rays, electron beams, etc. and can be used as an effective component of a curable resin composition. In the curable resin composition containing the present organopolysiloxane as an effective component, the predominant chain of the effective component comprises a siloxane bond, and thus cured products having the silicone characteristics such as a peelability, a surface lubricity, water and oil repellency, etc. can be obtained therefrom. Furthermore, the present organopolysiloxane has a relatively low molecular weight and thus has a higher compatibility with the (meth)acrylate compound than that of higher molecular weight resins. That is, curable resin compositions can be readily prepared, and furthermore cured products having good transparency and luster can be obtained from curable resin compositions containing various (meth) acrylate compounds. Particularly when the terminal silicons each of the siloxane chain of the organopolysiloxane have alkoxy groups and/or aryloxy groups, the compatibility with a (meth)acrylate compound is effectively more improved than that of organopolysiloxanes having no such groups. Furthermore, before or after the curing of resin, such alkoxy groups and/or aryloxy groups can be also used in further reaction.

The present organopolysiloxane can show distinguished curing characteristics when used together with a (meth) acrylate compound, and can be suitably used as a curable resin composition by mixing with a (meth)acrylate compound to adjust the viscosity or other properties.

The (meth)acrylate compound to be used together with the present organopolysiloxane may be the same (meth) acrylate compounds used in the production of the present organopolysiloxane or other (meth)acrylate compounds. The other (meth)acrylate compounds include, for example, phenol EO-modified (meth)acrylate, phenol PO-modified (meth)acrylate, nonylphenol EO-modified (meth)acrylate, nonylphenol PO-modified (meth)acrylate, 2-ethylhexylcarbitol (meth)acrylate, isobornyl (meth) acrylate, tetrahydrofurfuryl (meth)acrylate, hydroxyethyl (meth)acrylate, hydroxypropyl (meth)acrylate, hydroxybutyl (meth)acrylate, hydroxyhexyl (meth)acrylate, diethyleneglycol mono(meth)acrylate, dipropylglycol mono(meth) acrylate, triethyleneglycol mono(meth)acrylate, tripropyleneglycol mono(meth)acrylate, tetraethyleneglycol mono(meth)acrylate, 1,4-butanediol mono(meth)acrylate, 1,5-pentanediol mono(meth)acrylate, 1,6-hexanediol mono (meth)acrylate, 1,9-nonanediol mono(meth)acrylate, neopentylglycol mono(meth)acrylate, neopentylglycol EO-modified mono(meth)acrylate, neopentylglycol PO-modified mono(meth)acrylate, bisphenol A/EO-modified mono(meth)acrylate, bisphenol A/PO-modified mono(meth)acrylate, hydrogenated bisphenol A/EO-modified mono(meth)acrylate, hydrogenated bisphenol A/PO-modified mono(meth)acrylate, etc. These and those (meth)acrylate compounds mentioned before can be used alone or in combination of two or more thereof.

In the curable resin composition, a mixing ratio of the organopolysiloxane to the (meth)acrylate compound depends on desired applications and is not particularly limited, but preferably 0.1 to 90 parts by weight, more preferably 1 to 50 parts by weight, of the organopolysiloxane is used per 100 parts by weight of the (meth)acrylate compound. When the amount of the organopolysiloxane is less than 0.1 part by weight, the surface lubricity of the cured product may be unsatisfactory, whereas the amount of the organopolysiloxane exceeds 90 parts by weight, the hardness of the cured product would be lowered.

A means for curing the curable resin composition is not particularly limited, but heat curing, ultraviolet curing and electron beam curing are suitable. These ordinary curing means can be used as such in the curing.

The present organopolysiloxane can be cured by heat, ultraviolet rays, electron beams or the like, and the cured products have distinguished "silicone characteristics" such as a peelability, a surface lubricity, a water and oil repellency, etc. Since the present organopolysiloxane has a good compatibility with a (meth)acrylate compound, cured films having good transparency and luster as well as the above-mentioned distinguished silicone characteristics can be obtained from the present curable compositions comprising the present organopolysiloxane and optionally a (meth) acrylate compound. Thus, the present curable resin compositions are useful as a resin for mold-releasable paper, a coating agent, an anticorrosive agent for printed substrates, etc. The present process for producing the present organopolysiloxane has an easy reaction control and can produce organopolysiloxanes having a distinguished preservation stability, and thus has a remarkably important industrial value.

DESCRIPTION OF PREFERRED EMBODIMENTS

The present invention will be described in detail below, referring to Examples and Comparative Examples.

Synthesis of Starting Materials

Synthesis Example 1

Synthesis of organopolysiloxane having SiH groups only at both terminals thereof (synthesis of α,ω type polydimethylsiloxane according to the reaction shown by reaction equation (V), where $R^1$ and $R^4$ are each an ethoxy group; $R^2$ and $R^3$ are each a methyl group; and n is a positive number of about 18, the α,ω type polydimethylsiloxane being hereinafter referred to as "Silicone A")

The synthesis was carried out under the following conditions, using the following starting materials:

Starting Materials (1) Polydimethylsiloxane-α,ω-diol (commercially available from Toray-Dow Corning Silicone K.K., Japan; number average molecular weight: 1,272 in terms of polystyrene)

(2) Triethyoxysilane (commercially available from Toa Gosei Co. Ltd., Japan under trade name "TRIES")

Reaction Conditions

① 10.0 g (7.9 mmol) of polydimethylsiloxane-α,ω-diol was charged into a 4-necked 100 ml flask provided with a stirrer, a thermometer and a cooler, and then the flask was evacuated and then flushed with nitrogen.

② Then, the flask was heated to 60° C. and 15.0 g (92 mmol) of triethoxysilane was added thereto, and the resulting mixture was stirred while keeping the system at 60° C. to conduct reaction.

③ The progress of reaction was monitored by gas chromatography. After 6 hours from the start of reaction, the reaction was completed by confirming that there was no change in the composition ratio of the starting material triethoxysilane to the by-produced ethanol.

④ Excess triethoxysilane and the by-produced ethanol were removed from the resulting reaction solution under reduced pressure, and further volatile impurities were removed therefrom by heating in a vacuum atmosphere (60° to 70° C.; 0.01 torr) to obtain 11.8 g of a colorless, transparent viscous liquid.

IR chart and NMR chart of the liquid so obtained are shown in FIG. 1 and FIG. 2, respectively. In FIG. 1, the peak around 2, 200 cm$^{-1}$ shows the presence of hydrogen atom bonded to the terminal silicon. In FIG. 2, the peak at 3.8 ppm corresponds to the hydrogen atom bonded to the carbon atom adjacent to the oxygen in the ethoxy group bonded to the terminal silicon (Si-OCH$_2$), and the peak at 4.7 ppm corresponds to the hydrogen atom bonded to the terminal silicon (Si-H). From peak areas thereof it can be seen that a ratio of the number of ethoxy groups bonded to the terminal silicon to the number of hydrogen atoms bonded to the terminal silicon is 2:1. From these facts it was confirmed that silicone A, whose $R^1$ and $R^4$ are each an ethoxy group and whose $R^2$ and $R^3$ are each a methyl group in the formula (III), was synthesized.

EXAMPLE 1

The silicone A prepared in Synthesis Example 1 and large excess in moles of trimethylolpropane propyleneoxide-modified triacrylate (commercially available from Toa Gosei Co. Ltd., Japan under trade name of "ARONIX M-310") over the silicone A were charged into a reactor vessel flushed with nitrogen and heated with stirring in the presence of a platinum catalyst to produce organopolysiloxane A-1 having acryloyl groups at both terminals thereof. The reaction and the structure of organopolysiloxane A-1 are schematically shown by the following reaction equation (X):

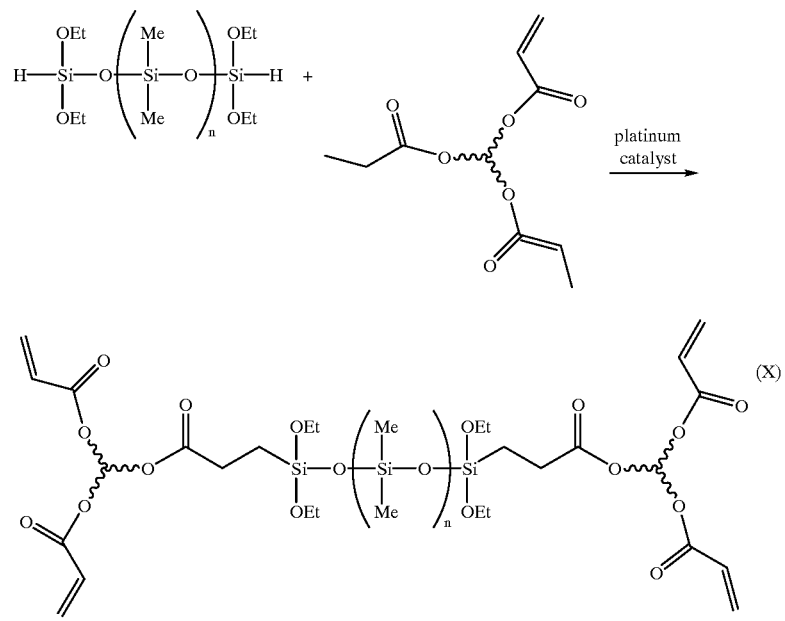

Since the organopolysiloxane A-1 has two acryloyl groups each at both terminals thereof, it is curable by irradiation with ultraviolet rays, heating or the like. Furthermore, it has alkoxy groups besides the acryloyl groups, and thus the alkoxy groups can be utilized in further reaction.

EXAMPLE 2

Trimethylolpropane PO-modified triacrylate was added to the silicone A prepared in Synthesis Example 1 under the following conditions to produce an organopolysiloxane A-2 having acryloyl groups at both terminals thereof.

① 3.0 g (2.1 mmol) of silicone A and 30.0 g (63.8 mmol) of trimethylolpropane PO-modified triacrylate (with 1 mole of PO added)(commercially available from Toa Gosei Co. Ltd., Japan under tradename "ARONIX M-310") were charged into a 100-ml reactor provided with a stirrer, a thermometer and a cooler, and then the reactor was evacuated and then flushed with nitrogen.

② After the reactor was heated to 70° C. to 80° C., 100 μl of a 0.05 M $PtCl_2$ $(C_6H_5CN)_2$ solution in benzonitrile was charged thereto, and the mixture was stirred, while keeping the reacator at 70° C. to 80° C. to carry out reaction.

③ After 6 hours from the start of reaction, volatile matters such as benzonitrile, etc. were removed therefrom by heating in a vacuum atmosphere, whereby a slightly yellowish, transparent curable resin composition B-1 comprising organopolysiloxane A-2 and excess of trimethylolpropane PO-modified triacrylate was obtained.

EXAMPLE 3

Trimethylolpropane PO-modified triacrylate (with a different number of moles of PO added from that of Example 2) was added to the silicone A prepared in Synthesis Example 1 to produce a curable resin (which will be hereinafter referred to as "organopolysiloxane A3").

That is, in Example 3, 30.0 g (46.5 mmol) of trimethylolpropane PO-modified triacrylate (with 2 moles of PO added) (commercially available from Toa Gosei Co. Ltd., Japan under tradename "ARONIX M-320") was used in place of trimethylolproapne PO-modified triacrylate (with 1 mole of PO added), while using other conditions and procedures same as in Example 2, whereby a slightly yellowish, transparent curable resin composition B-2 comprising organopolysiloxane A-3 and excess of trimethylopropane PO-modified triacrylate was obtained.

EXAMPLE 4

Trimethylolpropane allylether diacrylate was added to the silicone A prepared in Synthesis Example 1 to produce a curable resin (which will be hereinafter referred to as "organopolysiloxane A-4").

That is, in Example 4, 30.0 g (106.3 mmole) of trimethylolpropane allylether diacrylate was used in place of trimethylolpropane PO-modified triacrylate (with 1 mole of PO added) used in Example 2, while using other conditions and procedures same as in Example 2, whereby a slightly yellowish, transparent curable resin composition B-3 comprising the organopolysilone A-4 and excess of trimethylolpropane allylether diacrylate was obtained.

EXAMPLE 5

In place of polydimethylsiloxane-α,ω-diol having a number average molecular weight of 1,272 used in Synthesis Example 1, polydimethylsiloxane-α,ω-diol having a number average molecular weight as high as about 10,000 was used, while using other conditions and procedures same as in Synthesis Example 1, whereby α,ω type polydimethylsiloxane, whose $R^1$ and $R^4$ were each an ethoxy group and whose $R^2$ and $R^3$ were each a methyl group and whose n was about 130 in the formula (III) (which will be hereinafter referred to as "silicone a") was synthesized.

Trimethylolpropane PO-modified triacrylate with 1 mole of PO added) was added to silicone a having a higher molecular weight in place of silicone A, while using other conditions and procedures same as in Example 2 whereby a slightly yellowish, turbid curable resin composition b-1 comprising organopolysiloxane a-1 and excess of trimethylolpropane PO-modified triacrylate was obtained.

Evaluation of Curable Resin Compositions

3% by weight of a photoinitiator was added each to the curable resin compositions obtained in Examples 2 to 5 and the above-mentioned ARONIX M-310 (Comparative Example 1) and ARONIX M-320 (Comparative Example 2), and their ultraviolet curability and peelability of cured films were evaluated. As the photoinitiator, 2-hydroxy-2-methyl-1-phenylpropane-1-on (commercially available from Japan Ciba-Geigy K.K., Japan under tradename Darocure 1173) was used.

Film-Making Procedure

Substrate: Polycarbonate

Coating procedure: 20 μm bar coater

Conditions for Ultraviolet Irradiation

Lamp: 80 W/cm condenser-type high pressure mercury lamp

Lamp level: 10 cm

Conveyor speed: 10 m/min

Curability

The curable resin composition-coated substrates were passed under the ultraviolet lamp under the above-mentioned condition by 10 repetitions and then the curing state of the compositions was evaluated by the following 4 scores:

◎: Good (without any surface tackiness)

o: Substantially good (with slight surface tackiness)

Δ: Somewhat poor (with surface tackiness)

X: No curing

Peelability

A pressure-sensitive adhesive tape was applied on the surface of the cured film with fingers and peeled off with fingers immediately after the application.

According to degrees of feeling of the finger force required for peeling the applied adhesive tape off the substrate, peelability was evaluated by the following three scores: o: weak (high peelability), Δ: medium, X: strong (low peelability)

Results of evaluation are shown in the following Table 1.

TABLE 1

|  | Appearance | Curability | State of cured film | Peelatility |
|---|---|---|---|---|
| Example 2 | Slightly yellowish, transparent | ⊙ | Colorless, transparent | ○ |
| Example 3 | Slightly yellowish, transparent | ⊙ | " | ○ |
| Example 4 | Slightly yellowish, transparent | ○ | " | ○ |
| Example 5 | Slightly yellowish, turbid | Δ | White turbid with bleeding | ○ |
| Comp. Ex. 1 | Slightly yellowish, transparent | ⊙ | Colorless, transparent | x |
| Comp. Ex. 2 | Slightly yellowish, transparent | ⊙ | " | x |

As is apparent from Table 1, all the curable resin compositions of Examples 2 to 4 had a good or substantially good curability. Even the curable resin composition of Example 4 could be cured to a state free from the surface tackiness by passing under the lamp by additional 5 repetitions. The fact that the curable resin compositions and their cured films were transparent, reveals that the organopolysiloxanes A-2 to A-4 had a good compatibility with acrylate compounds M-310, M-320 and trimethylolpropane allylether diacrylate. The cured films obtained from the resin compositions of Examples 2 to 4 were given the silicone characteristics by the organopolysiloxanes A-2 to A-4, and thus had a considerably better peelability than that of the cured film made only from M-310 or M-320. From the good curability and no presence of bleeding, etc. on the surfaces of the cured films, it can be presumed that acryloyl groups are introduced into at least most of silicones.

In Example 5 using the high molecular weight silicone, on the other hand, the organopolysiloxane a-1 was somewhat less compatible with M-310, and thus the curable resin composition b-1 and its cured film were both turbid. There was some silicone bleeding on the surface of the cured film, which shows that there remained some silicones having no acryloyl groups introduced therein.

The curable resin composition b-1, when left standing for one day, was separated into a lower layer consisting mainly of excess of the trimethylolpropane PO-modified triacrylate and a slightly yellowish, turbid upper layer consisting mainly of the organopolysiloxane a-1.

Synthesis of Starting Materials

Synthesis Example 2

Synthesis of Trimethylolpropane Triacrylatetriethoxy Silane Adduct 100 g (0.34 mol) of trimethylolpropane triacrylate, 50 ml of toluene and 0.016 g of $PtCl_2(C_6H_5CN)_2$ were charged into a 300-ml, 4-necked flask provided with a stirrer, a thermometer, a cooler, a dropping funnel and an air bubbler, and then the flask was heated to 60° C. After the reaction system reached 60° C., 66.5 g (0.41 mol) of triethoxysilane was dropwise added thereto over one hour, and reaction was continued at 60° C. for further 5 hours. After the end of reaction, toluene and unreacted triethoxysilane were distilled off, whereby the desired product was obtained.

Analysis of the reaction product by gas chromatography (which will be hereinafter referred to as "GC") revealed no presence of trimethylolpropane triacrylate as the starting material. $^1$H-NMR analysis thereof revealed the presence of 1.9 acryloyl groups in one molecule.

Synthesis Example 3

Synthesis of Ditrimethylolpropane Tetracrylatetriethoxy Silane Adduct 100 g (0.22 mol) of ditrimethylolpropane tetracrylate, 50 ml of toluene, and 0.015 g of $PtCl_2(C_6H_5CN)_2$ were charged into a 300-ml 4-necked flask provided with a stirrer, a thermometer, a cooler, a dropping funnel and an air bubbler, and then the flask was heated to 60° C. After the reaction system reached 60°60 C., 42.3 g (0.26 mol) of triethoxysilane was dropwise added thereto over one hour, and reaction was continued at 60° C. for further 5 hours. After the end of reaction, toluene and unreacted triethoxysilane were distilled off, whereby the desired product was obtained.

GC analysis of the reaction product revealed no presence of ditrimethylolpropane tetracrylate as the starting material, and $^1$H-NMR analysis thereof revealed the presence of 2.8 acryloyl groups in one molecule.

EXAMPLE 6

20 g of the trimethylolpropane triacrylatetriethoxysilane adduct obtained in Synthesis Example 2, 27.6 g of dimethylpolysiloxane with both terminal silanols (commercially available from Toray-Dow Corning Silicone K.K., Japan; number average molecular weight: 1,270 in terms of polystyrene), 0.2 g of p-toluenesulfonic acid and 48 g of methylethylketone were charged into a 300-ml, 4-necked flask provided with a stirrer, a thermometer, a cooler and an air bubbler, and subjected to reaction at 60° C. for 4 hours. Formation of ethanol could be confirmed during the reaction by GC analysis. After the end of reaction, the reaction mixture was cooled to room temperature and neutralized with an anion exchange resin, and the solvent was distilled off, whereby organopolysiloxane having acryloyl groups at both terminals (which will be hereinafter referred to as "organopolysiloxane B") was obtained.

EXAMPLE 7

20 g of trimethylolpropane triacrylatetriethoxysilane adduct synthesized in Synthesis Example 2, 34.7 g of methylphenylpolysiloxane with both terminal silanols (commercially avaible from Toshiba Silicone K.K. Japan under tradename YF3804), 0.2 g of p-toluenesulfonic acid and 55 g of methylethylketone were charged into a 300-ml, 4-necked flask provided with a stirrer, a thermometer, a cooler and an air bubbler, and subjected to reaction at 60° C. for 4 hours. Formation of ethanol could be confirmed during the reaction by GC analysis. After the end of reaction, the reaction mixture was cooled to room temperature and neutralized with an anion exchange resin, and the solvent was distilled off, whereby organopolysiloxane having acryloyl groups at both terminals (which will be hereinafter referred to as "organopolysiloxane C") was obtained.

EXAMPLE 8

20 g of ditrimethylolpropane tetracrylatetriethoxysilane adduct obtained in Synthesis Example 3, 18.2 g of dimethylpolysiloxane with both terminal silanols (commercially available from Toray-Dow Corning Silicone K.K., Japan; number average molecular weight: 1,270 in terms of polystyrene), 0.1 g of p-toluenesulfonic acid, 4 g of toluene, and 40 g of methyl ethyl ketone were charged into a 300-ml, 4-necked flask provided with a stirrer, a thermometer, a cooler and an air bubbler and subjected to reaction at 60° C. for 4 hours. Formation of ethanol could be confirmed during the reaction by GC analysis. After the end of reaction, the reaction mixture was cooled to room temperature, neutralized with an anion exchange resin, and the solvent was distilled off, whereby organopolysiloxane having acryloyl groups at both terminals (which will be hereinafter referred to as "organopolysiloxane D") was obtained.

EXAMPLE 9

20 g of ditrimethylolpropane tetracrylatetriethoxysilane adduct synthesized in Synthesis Example 3, 22.9 g of methylphenylpolysiloxane with both terminal silanols (commercially available from Toshiba-Silicone K.K., Japan under tradename YE3804], 0.1 g of p-toluenesulfonic acid, 4 g of toluene and 40 g of methylethylketone were charged into a 300-ml, 4-necked flask provided with a stirrer, a thermometer, a cooler and an air bubbler, and subjected to reaction at 60° C. for 4 hours. Formation of ethanol could be confirmed during the reaction by GC analysis. After the end of reaction, the reaction mixture was cooled to room temperature and neutralized with an anion exchange resin, and the solvent was distilled off, whereby organopolysiloxane having acryloyl groups at both terminals (which will be hereinafter referred to as "organopolysiloxane E") was obtained.

EXAMPLES 10 TO 16 AND COMPARATIVE EXAMPLES 3 TO 4

The organopolysiloxanes of Examples 6 to 9 were mixed with tripropyleneglycol diacrylate (commercially available from Toa Gosei Co. Ltd., Japan under trademark ARONIX M-220) or trimethylolpropane triacrylate (commercially available from Toa Gosei Co. Ltd., Japan under tradename ARONIX M-308) as an acrylate compound in mixing ratios shown in the following Table 2. Furthermore, 5 parts by weight of 2-hydroxy-2-methyl-1-phenylpropane-1-on (commercially available from Japan Ciba-Geigy K.K., Japan under tradename Darocure 1173) was added thereto as a photoiniator per 100 parts by weight of total amount of the organopolysiloxane and the acrylate compound to prepare curable resin compositions. Comparative Examples 3 and 4 contained no organopolysiloxane at all.

These compositions were applied to iron plates to a thickness of 10 μm and cured under the following conditions.

Kinetic friction coeffients and contact angles to water and hexadecane of the cured products were measured. The results are shown in the following Table 3.

Curing Conditions 80 W/cm high pressure mercury lamp at a lamp level of 10 cm; conveyor speed: 10 m/min and number of passes: 5 passes.

Procedures for Measurement

Kinetic friction coefficient: Kinetic friction coefficient of a stainless steel ball under a load of 100 g at a moving speed of 1,000 mm/min was measured with a surface meter made by Shinto Kagaku K.K., Japan.

Contact angle was measured in the ordinary procedure, using a contact angle meter made by Emul K.K., Japan.

TABLE 2

| | Organopolysiloxane (wt. %) | | | | M-200 | M-308 |
|---|---|---|---|---|---|---|
| | B | C | D | E | (wt. %) | (wt. %) |
| Example 10 | 50 | | | | 50 | |
| Example 11 | | 10 | | | 90 | |
| Example 12 | | 10 | | | | 90 |
| Example 13 | | | 10 | | 90 | |
| Example 14 | | | 10 | | | 90 |
| Example 15 | | | | 10 | 90 | |
| Example 16 | | | | 10 | | 90 |
| Comp. Ex. 3 | | | | | 100 | |
| Comp. Ex. 4 | | | | | | 100 |

TABLE 3

| | Kinetic friction coefficient | Contact angle (degree) | |
|---|---|---|---|
| | | Wter | Hexadecane |
| Example 10 | 0.042 | 101 | 39 |
| Example 11 | 0.082 | 98 | 35 |
| Example 12 | 0.090 | — | — |
| Example 13 | 0.049 | 105 | 40 |
| Example 14 | 0.071 | — | — |
| Example 15 | 0.072 | 102 | 39 |
| Example 16 | 0.86 | 98 | 40 |
| Comp. Ex. 3 | 0.290 | 89 | 24 |
| Comp. Ex. 4 | 0.250 | 80 | 22 |

What is claimed is:

1. An organopolysiloxane having acryloyl groups or methacryloyl groups at both terminals thereof, obtainable by reacting an organopolysiloxane having Si-H termination with the double bonds of the acryloyl groups or methacryloyl groups of a compound having at least two acryloyl groups or methacryloyl groups, by way of hydrosilylation.

2. An organopolysiloxane according to claim 1, represented by the following structural formula (I):

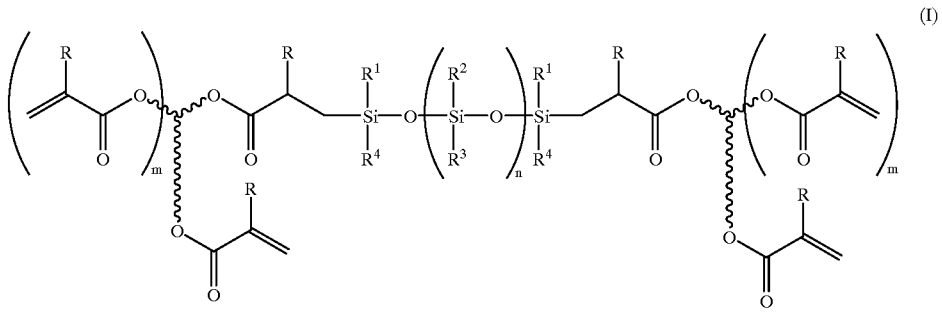

where the wavy lines extending from the O atoms and meeting at a point designate a residual group formed by removing (meth)acrylovloxy groups from a (meth)acrylate compound; R is a methyl group or a hydrogen atom; $R^1$ and $R^4$ are each independently an alkoxy group, an aryloxy group, an alkyl group, a cycloalkyl group or an aryl group; $R^2$ and $R^3$ are each independently an alkyl group, a cycloalkyl group or an aryl group; n is a positive number of 1 to 10,000; and m is 0 or a positive number of at most 10.

3. An organopolysiloxane according to claim 1, represented by the following structural formula (II):

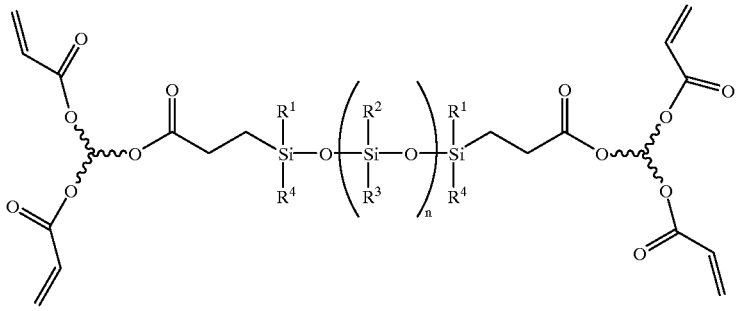

where the wavy lines extending from the O atoms and meeting at a point designate a residual group formed by removing acryloyloxy groups from an acrylate compound; $R^1$ and $R^4$ are each independently an alkoxy group, an aryloxy group, an alkyl group, a cycloalkyl group or an aryl group; $R^2$ and $R^3$ are each independently an alkyl group, a cycloalkyl group or an aryl group; and n is a positive number of 1 to 10,000.

4. A process for producing an organopolysiloxane having acryloyl groups or methacryloyl groups at both terminals thereof, which comprises adding a compound having at least two acryloyl groups or methacryloyl groups to an organopolysiloxane represented by the following structural formula (III);

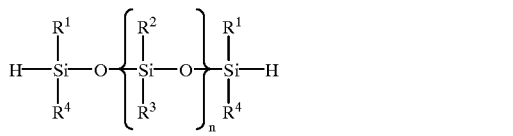

where $R^1$ and $R^4$ are each independently an alkoxy group, an aryloxy group, an alkyl group, a cycloalkyl group or an aryl group; $R^2$ and $R^3$ are each independently an alkyl group, a cycloalkyl group or an aryl group; n is a positive number of 1 to 10,000. in the presence of a catalyst thereby to effect hydrosilylation reaction.

5. An organopolysiloxane according to claim 2, wherein $R^1$ is an alkoxy group or an aryloxy group.

6. An organopolysiloxane according to claim 2, wherein $R^1$ and $R^4$ are each independently an alkoxy group or an aryloxy group.

7. An organopolysiloxane according to claim 2, wherein n is a positive number of 10 to 100.

8. An organopolysiloxane according to claim 3, wherein $R^1$ is an alkoxy group or an aryloxy group.

9. An organopolysiloxane according to claim 3, wherein $R^1$ and $R^4$ are each independently an alkoxy group or an aryloxy group.

10. An organopolysiloxane according to claim 3, wherein n is a positive number of 10 to 100.

11. A process according to claim 4, wherein $R^1$ and $R^4$ are each independently an alkoxy group or an aryloxy group.

12. A process according to claim 4, wherein n is a positive number of 10 to 100.

13. A curable resin composition, which comprises an organopolysiloxane having acryloyl groups or methacryloyl groups at both terminals thereof, obtainable by reacting an organopolysiloxane having Si-H termination with the double bonds of the acryloyl groups or methacryloyl groups of a compound having at least two acryloyl groups or methacryloyl groups, by way of hydrosilylation.

14. A curable resin composition which comprises an organopolysiloxane represented by the following structural formula (I):

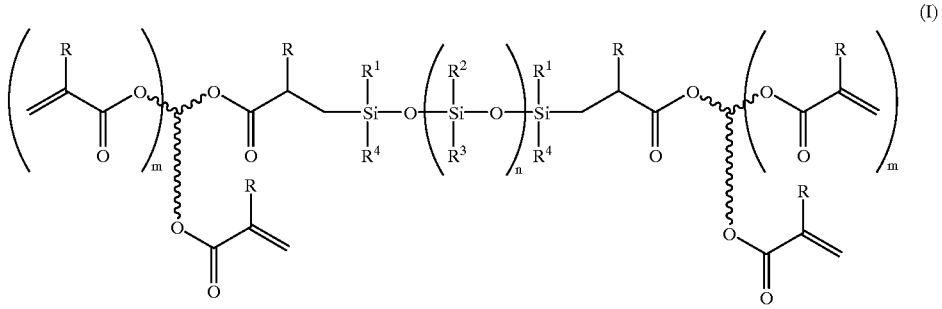

where the wavy lines extending from the O atoms and meeting at a point designate a residual group formed by removing (meth)acryloyloxy groups from a (meth)acrylate compound; R is a methyl group or a hydrogen atom; $R^1$ and $R^4$ are each independently an alkoxy group, an aryloxy group, an alkyl group, a cycloalkyl group or an aryl group; $R^2$ and $R^3$ are each independently an alkyl group, a cycloalkyl group or an aryl group; n is a positive number of 1 to 10,000; and m is 0 or a positive number of at most 10.

15. A curable resin composition which comprises an organopolysiloxane represented by the following structural formula (II):

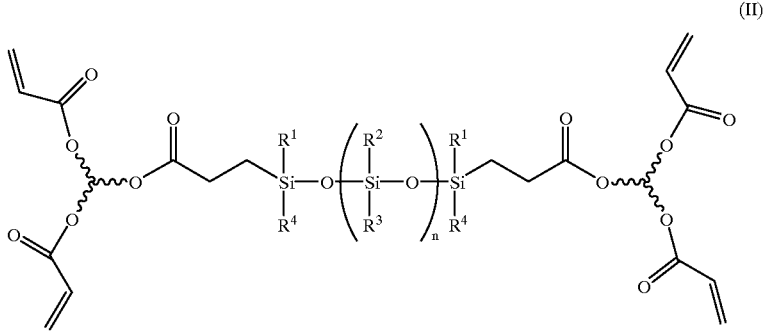

where the wavy lines extending from the O atoms and meeting at a point designate a residual group formed by removing acryloyloxy groups from an acrylate compound; $R^1$ and $R^4$ are each independently an alkoxy group, an aryloxy group, an alkyl group, a cycloalkyl group or an aryl group; $R^2$ and $R^3$ are each independently an alkyl group, a cycloalkyl group or an aryl group; and n is a positive number of 1 to 10,000.

16. A curable resin composition according to claim 14, wherein $R^1$ and $R^4$ are each independently an alkoxy group on an aryloxy group.

17. A curable resin composition according to claim 14, wherein n is a positive number of 10 to 100.

18. A curable resin composition according to claim 15, wherein $R^1$ and $R^4$ are each independently an alkoxy group or an aryloxy group.

19. A curable resin composition according to claim 15, wherein n is a positive number of 10 to 100.

20. A process according to claim 4, wherein the catalyst is a catalyst of the Group VIII metal.

21. A process according to claim 20, wherein the catalyst of the Group VIII metal is selected from the group consisting of metallic simple substances, organometallic complexes, metallic salts and metallic oxides of the Group VIII metal.

22. A process according to claim 21, wherein the the Group VIII metal is platinum.

23. A process according to claim 21, wherein the catalyst of the Group VIII metal is selected from organoplatinum complexes.

* * * * *